US012662660B2

(12) United States Patent
Zhang

(10) Patent No.: US 12,662,660 B2
(45) Date of Patent: Jun. 23, 2026

(54) METHODS FOR AMPLIFYING AND DIFFERENTIATING PANCREATIC CELLS, AND APPLICATION THEREOF

(71) Applicants:SHANGHAI CELLIVER BIOTECHNOLOGY CO., LTD., Shanghai (CN); SHANGHAI CRYOWISE MEDICAL TECHNOLOGY CO., LTD., Shanghai (CN)

(72) Inventor: Hongdan Zhang, Shanghai (CN)

(73) Assignees: SHANGHAI CELLIVER BIOTECHNOLOGY CO., LTD., Shanghai (CN); SHANGHAI CRYOWISE MEDICAL TECHNOLOGY CO., LTD., Shanghai (CN)

( * ) Notice: Subject to any disclaimer, the term of this patent is extended or adjusted under 35 U.S.C. 154(b) by 1038 days.

(21) Appl. No.: 17/776,594

(22) PCT Filed: Apr. 1, 2021

(86) PCT No.: PCT/CN2021/085019
§ 371 (c)(1),
(2) Date: May 12, 2022

(87) PCT Pub. No.: WO2021/204061
PCT Pub. Date: Oct. 14, 2021

(65) Prior Publication Data
US 2022/0389387 A1 Dec. 8, 2022

(30) Foreign Application Priority Data

Apr. 9, 2020 (CN) .......................... 202010276073.9
Mar. 30, 2021 (CN) .......................... 202110343020.9

(51) Int. Cl.
*C07K 14/62* (2006.01)
*C12N 5/071* (2010.01)

(52) U.S. Cl.
CPC ........... *C12N 5/0676* (2013.01); *C07K 14/62* (2013.01); *C12N 2501/10* (2013.01); *C12N 2501/335* (2013.01); *C12N 2501/91* (2013.01); *C12N 2501/999* (2013.01)

(58) Field of Classification Search
CPC ............... C12N 5/0678; C12N 5/0676; C12N 2501/10; C12N 2501/999
See application file for complete search history.

(56) References Cited

U.S. PATENT DOCUMENTS 9,752,124 B2 * 9/2017 Sato ..................... C12N 5/0679

FOREIGN PATENT DOCUMENTS

CN 108330099 A 7/2018
WO WO-0047720 A2 * 8/2000 ................ A61P 5/48

OTHER PUBLICATIONS

Li WC, Chen CY, Kao CW, Huang PC, Hsieh YT, Kuo TY, Chen TY, Chia HY, Juang JH. Porcine Neonatal Pancreatic Cell Clusters Maintain Their Multipotency in Culture and After Transplantation. Sci Rep. May 29, 2018;8(1):8212. doi: 10.1038/s41598-018-26404-6. PMID: 29844347; PMCID: PMC5974285. (Year: 2018).*

Yu-Ree Cho , Sang-Duk Kim , Hyo-Ihl Chang , Ha-Chin Sung , Cherl-Ho Lee and Chan-Wha Kim. A Method for the Separation of Mouse Pancreatic Islets Using Discontinuous Percoll Gradient Centrifugation. J. Microbiol. Biotechnol. 1999; 9(4): 522-524 (Year: 1999).*

Lidgerwood GE, Pitson SM, Bonder C, Pébay A. Roles of lysophosphatidic acid and sphingosine-1-phosphate in stem cell biology. Prog Lipid Res. Oct. 2018; 72:42-54. doi: 10.1016/j.plipres.2018.09.001. Epub Sep. 6, 2018. PMID: 30196008. (Year: 2018).*

Serafimidis I, Heximer S, Beis D, Gavalas A. G protein-coupled receptor signaling and sphingosine-1-phosphate play a phylogenetically conserved role in endocrine pancreas morphogenesis. Mol Cell Biol. Nov. 2011;31(22):4442-53. doi: 10.1128/MCB.05702-11. Epub Sep. 12, 2011. (Year: 2011).*

* cited by examiner

*Primary Examiner* — Fereydoun G Sajjadi
*Assistant Examiner* — Qinhua Gu

(57) ABSTRACT

An amplifying method of pancreatic cells is provided. The amplifying method includes performing digestion, resuspension, discontinuous density gradient centrifugation treatment and amplifying treatment sequentially. The mammalian pancreatic duct is used as the source of pancreatic precursor-like cells in the amplifying method, and islet cells and acinar cells in the cell clusters obtained by the discontinuous density gradient centrifugation treatment are removed. It is beneficial to improve the yield of the pancreatic precursor-like cells availably, and avoid the ethical restrictions and possible carcinogenic risks caused by using the embryonic stem cells. The amplifying medium used comprises a reprogramming substance composed of several small molecule compounds. It can avoid the risks of non-specific and off-target deletion that are easily caused by the use of the gene-editing methods to change the gene sequence. Also provided is a differentiation method and an application of the pancreatic precursor-like cells obtained by the amplifying method.

9 Claims, 5 Drawing Sheets

METHODS FOR AMPLIFYING AND DIFFERENTIATING PANCREATIC CELLS, AND APPLICATION THEREOF

TECHNICAL FIELD

This invention relates to the field of biotechnology, in particular to methods for amplifying and differentiating pancreatic cells, and applications thereof.

BACKGROUND ART

Diabetes mellitus is a chronic metabolic disorder characterized by hyperglycemia caused by insufficient insulin secretion or insulin resistance in surrounding tissues. The late stage of diabetes can cause damage to the whole body tissue, especially the eyes, kidneys, cardiovascular and nerves system, as well as dysfunction and organ failure. Currently, drug therapy and insulin supplementation are the most common treatments for diabetes, but the treatments cannot completely cure diabetes. Moreover, it is difficult to prevent from developing the long term complications.

Human β cells can secrete insulin to lower blood sugar to further regulate the fat and protein metabolism. Human embryonic stem cells have infinite proliferation capacity and can produce infinite human β cells theoretically, so they have attracted much attention in recent years. In the prior arts, embryonic stem cells are gradually induced to obtain cells with insulin secretion function, but the induction is complicated, long-cycle and high-cost. In addition, in the cell cluster induced by embryonic stem cells, the proportion of cells with insulin secretion function generally does not exceed 30%. The later purification process easily contaminates the cell cluster, so that the cells with insulin secretion function have potential carcinogenic risks. Therefore, it is urgent to find effective replacement cells for islet cells and obtain sufficient seed cells that can used for cell replacement therapy.

As a result, it is necessary to develop a new method for amplifying and differentiating pancreatic cells to solve the above-mentioned problems in the prior arts.

SUMMARY OF THE INVENTION

The purpose of this invention is to provide a method for amplifying and differentiating pancreatic cells, and applications thereof, so as to provide a good replacement choice to islet cells and avoid the ethical restrictions and possible carcinogenic risks resulting from embryonic stem cells-derived therapy in the prior arts, and the risks of non-specific and off-target deletion that are easily caused by the use of the gene-editing methods to change the gene sequence.

To achieve the above purposes, an amplifying method of pancreatic cells of this invention comprises the steps as follows:

S1: Obtaining pancreatic tissue, derived from a mammalian pancreatic duct;

S2: Performing digestion, resuspension, and discontinuous density gradient centrifugation treatment to the pancreatic tissue in sequence, collecting the cell clusters at each density gradient junction, and then removing islet cells and acinar cells in the cell clusters to obtain primary cells;

S3: Performing an amplifying treatment to the primary cells with an amplifying medium to induce reprogramming of the primary cells to obtain pancreatic precursor-like cells;

The amplifying medium comprises a reprogramming substance composed of several small molecule compounds, and the reprogramming substance comprises growth factor, Rock signal pathway inhibitor, WNT signal pathway agonist and TGF-β signal pathway inhibitor.

The beneficial effects of the amplifying method of this invention are as follows. The mammalian pancreatic duct is used as the source of the pancreatic precursor-like cells. After performing the discontinuous density gradient centrifugation treatment, the islet cells and acinar cells in the cell clusters are removed to ensure that most of the primary cells are pancreatic ductal epithelial cells to improve the yield of the pancreatic precursor-like cells as well as avoid the ethical restrictions and possible carcinogenic risks caused by the use of embryonic stem cells. In addition, in the step S3, the amplifying medium comprises a reprogramming substance composed of several small molecule compounds. The reprogramming substance comprises a growth factor, a Rock signal pathway inhibitor, a WNT signal pathway agonist, and a TGF-β signal pathway inhibitor. The reprogramming substance can induce the primary cells with a reprogramming approach to obtain the pancreatic precursor-like cells. It can avoid the risks of non-specific and off-target deletion that are easily caused by the use of gene-editing methods to change the gene sequence.

Preferably, the pancreatic tissue is derived from a human pancreatic duct.

Preferably, the growth factor comprises at least one of epidermal growth factor, hepatocyte growth factor, and fibroblast growth factor. In the amplifying medium, any one of the epidermal growth factor, the hepatocyte growth factor, and the fibroblast growth factor is 5-100 ng/ml. The beneficial effect is to promote the primary cells to differentiate into the pancreatic precursor-like cells with advantage.

Preferably, the Rock signal pathway inhibitor is 2-15 μmol/L, the WNT signal pathway agonist is 2-10 μmol/L, and the TGF-β signal pathway inhibitor is 0.5-20 μmol/L in the amplifying medium. The beneficial effect is to promote the proliferation of the primary cells availably.

Further preferably, the Rock signal pathway inhibitor is at least one of Y27632, Fasudil, Thiazovivin, and SB-772077-B. The WNT signal pathway agonist is at least one of recombinant WNT protein, recombinant R-spondin protein, and glycogen synthase kinase 3β inhibitor. The glycogen synthase kinase 3β inhibitor is at least one of BIO, CHIR99021, and TWS119. The TGF-β signal pathway inhibitor is at least one of A83-01, RepSox, and SB431542.

Preferably, the amplifying medium further comprises a basic medium, serum, and serum-free neuron supplement. In the amplifying medium, the total volume of the serum and the serum-free neuron supplement is not higher than 15%, and the volume percentage of the serum is 2-10%.

Further preferably, the reprogramming substance further comprises a lipid signal substance having a content of 0.5-10 μmol/L in the amplifying medium.

Further preferably, the lipid signal substance is at least one of sphingosine-1-phosphate and lysophosphatidic acid.

Further preferably, the basic medium is at least one of MEM, DMEM, BME, DMEM/F12, RPMI1640, CMRL1066, WilliamE, Neurobasal, and Fischers medium. The serum is fetal bovine serum. The serum-free neuron supplement is at least one of N2 supplement and B27 supplement.

Preferably, in the step S2, at least three demixing agents with different densities are used to perform the discontinuous density gradient centrifugation treatment, and the adjacent demixing agents are a low-density demixing agent and a high-density demixing agent. The density of the low-density demixing agent is decreased by 0.1-3% relative to the density of the high-density stratification. The beneficial effect is to make most pancreatic ductal epithelial cells exist at the junction between adjacent density gradients.

Further preferably, in the step S2, the at least three demixing agents with different densities, the highest density of the demixing agents is not higher than 1.1 g/ml, and the lowest density of the demixing agents is not less than 1.03 g/ml.

The differentiation method of the pancreatic precursor-like cells of this invention includes that the pancreatic precursor-like cells are inoculated in a culture dish, and then the pancreatic precursor-like cells are induced to differentiate into islet-like cells with a differentiation medium.

The beneficial effect of the differentiation method of this invention is to obtain good replacement cells for islet cells since the pancreatic precursor-like cells are obtained by the amplifying method of this invention.

Preferably, the differentiation medium comprises several small molecule inducers, and the several small molecule inducers comprise heparin, deacetylase inhibitor, ALK5 inhibitor, T3, and GLP-1 receptor agonist. The beneficial effect is to availably induce the differentiation of the pancreatic precursor-like cells into the islet-like cells with good islet functions.

Further preferably, the deacetylase inhibitor is at least one of nicotinamide and Trichostatin A. The GLP-1 receptor agonist is at least one of glucagon-like peptide-1, and Exendin-4.

Further preferably, the differentiation medium also comprises a basic medium and a serum-free neuron supplement. The basic medium is at least one of MEM, DMEM, BME, DMEM/F12, RPMI1640, CMRL1066, WilliamE, Neurobasal, and Fischers medium. The serum-free neuron supplement is at least one of N2 supplement and B27 supplement.

Further preferably, in the differentiation medium, the content of the heparin is 5-15 µg/ml, the content of the deacetylase inhibitor is 5-15 mmol/L, the content of the ALK5 inhibitor is 5-15 µmol/L, the content of the T3 is 0.5-2 µmol/L, and the content of the GLP-1 receptor agonist is 10-50 nmol/L.

This invention further provides an application of the islet-like cells obtained by the differentiation method. The application includes: the islet-like cells are applied to secreting insulin with high-glucose reagent in vitro; after the islet-like cells are applied to a mammalian model for 8 week, the body weight change rate of the mammalian model is −5% to +5%, and the blood sugar value is 10-20 mmol/L.

DESCRIPTION OF THE PREFERRED EMBODIMENTS

Figure 1:
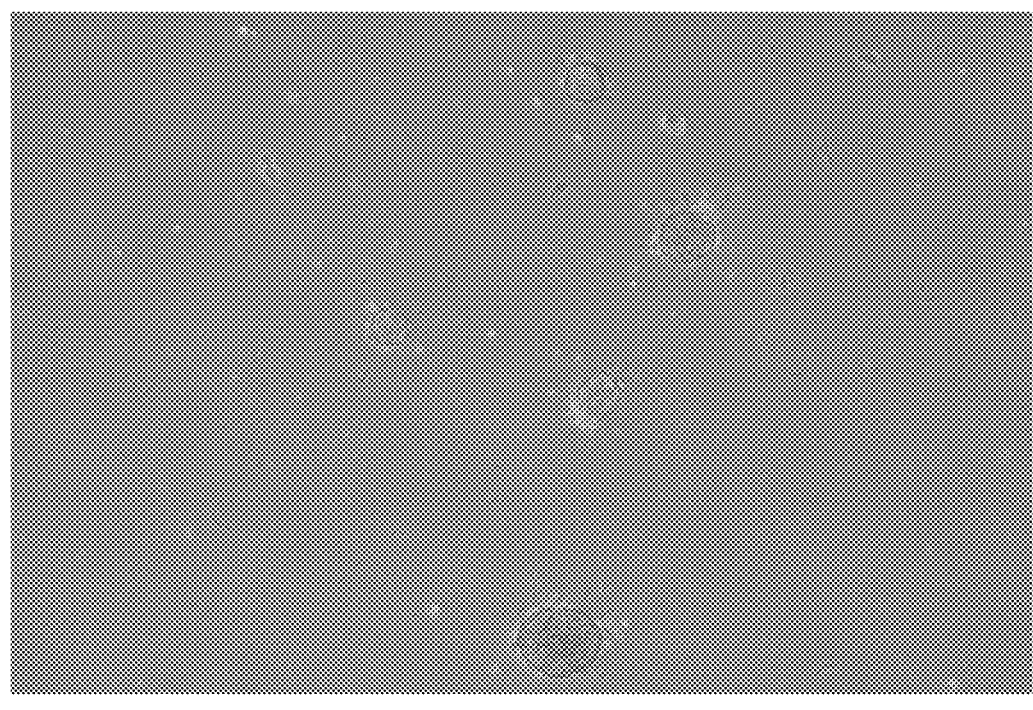
FIG. 1 is a photo of the proliferation of the primary cells of an example of this invention on $1^{st}$ day after adding the amplifying medium.

To make the objectives, technical solutions and advantages of this invention clearer, the technical solutions in the embodiments of this invention will be described clearly and completely with reference to the accompanying drawings of this invention. Obviously, the described embodiments are part of, but not all of, the embodiments of this invention. Based on the embodiments of this invention, all other embodiments obtained by those skilled in the art without creative work shall fall within the protection scope of this invention. Unless otherwise defined, the technical or scientific terms used herein shall have the usual meanings understood by those skilled in the art related to this invention. As used herein, "comprising" and other similar terms mean that the elements or objects appearing before the term encompass the elements or objects listed after the term and their equivalents, without excluding other elements or objects.

In the prior arts, although embryonic stem cells can be used to obtain single hormone-secreting cells with similar morphology and function to human pancreatic β-cells, which express mature β-cells markers, such as PDX1, MAFA, Insulin, etc. After the single hormone-secreting cells are transplanted into the immunodeficient diabetic mice, the hyperglycemia is partially reversed. However, the function and the transcription level are still different from the real β-cells, and potential oncogenicity and ethical issues also restrict the applications in humans. Other β-like cells, transformed from non-islet cells, such as gastrointestinal epithelial cells, hepatocytes, are quite different from human β-cells in molecular and functional properties, exist an epigenetic unstable state.

In view of the problems in the prior arts, some embodiments of this invention provide an amplifying method of pancreatic cells and a differentiating method of pancreatic-like cells obtained by the amplifying method.

The main sources of the reagents in embodiments of this invention are as follows:

Collagenase V, Ficoll, Percoll, streptozocin, dithizone, heparin, nicotinamide, fetal bovine serum, and T3 were from Sigma Co., Ltd. HBSS buffer and Hanks solution were form Beyotime Biotechnology Co., Ltd. DMEM/F12 was from Shanghai Basalmedia Technologies Co., Ltd. N2 supplement, B27 supplement and Y27632 were from Thermo Fisher Scientific Inc. Epidermal growth factor, hepatocyte growth factor and human fibroblast growth factor were from PeproTech Co., Ltd. Thiazovivin, SB431542, BIO, CHIR99021, sphingosine-1-phosphate, lysophosphatidic acid, A83-01, ALK5 inhibitor II and GLP-1 were from Topscience Co., Ltd. Transferrin, insulin, and Accutase cell detachment solution were from Shanghai Yeasen Biotechnology Co., Ltd.

GraphPad Prism 7 was used for all statistical analysis in the embodiments of this invention. In order to compare two averages, a two-tailed unpaired t-test was used to calculate statistical significance. In order to compare multiple values, one-way ANOVA and Dunnett correction were used together to compare multiple values with a single value. When the multiple values were compared with each other, Tukey was performed to correct. A P-value less than 0.05 was considered statistically significant.

The amplifying method comprises the steps as follows:

S1: Obtaining pancreatic tissue, derived from a mammalian pancreatic duct.

S2: After the pancreatic tissue was performed digestion, resuspension, and discontinuous density gradient centrifugation treatment in sequence, the cell clusters at each density gradient junction were collected. Then, islet cells and acinar cells in the cell clusters were removed to obtain primary cells.

S3: Performing an amplifying treatment to the primary cells with an amplifying medium to induce reprogramming of the primary cells to obtain pancreatic precursor-like cells.

The pancreas is responsible for the endocrine and exocrine function of a human body. The exocrine glands of the pancreas are composed of acini and ducts, which are responsible for secreting and expelling pancreatic juice to assist digestion. The endocrine glands are composed of pancreatic islets and are responsible for regulating the body's stable glucose level. Usually, the endocrine cells in islets are continuously differentiated from pancreatic ductal stem cells, and there are studies shown that pancreatic duct are the source of new islets under certain pathological conditions. In the step S1 of an embodiment of this invention, the pancreatic tissue was derived from the mammalian pancreatic duct. It was beneficial that the cells with good islet function obtained by the amplifying method and the differentiation method.

In some embodiments of this invention, the mammalian pancreatic duct did not have pathological changes.

In examples 1-3 of this invention, the mammal was a human, and the pancreatic tissue was derived from a human pancreatic duct.

Specifically, the human pancreatic duct did not have pathological changes.

In the step S2 of some embodiments of this invention, the digestion reagent used for the digestion comprises Collagenase V.

In the examples 1-3 of this invention, the digestion reagent was an HBSS buffer containing Collagenase V, and every 100 ml of the digestion reagent contains 1 gram of the Collagenase V.

Specifically, after the pancreatic tissue was washed repeatedly with normal saline containing 10% bi-antibody to remove blood stains, it was cut into pieces about 1 cm$^3$, and the 5 times volume of the digestion reagent was added. Afterwards, the pancreatic tissue was placed in a thermostatic shaking water bath at 37° C. at a rate of 120 revolutions per minute for 30 minutes to perform the digestion. Then, the digestion was terminated by using the HBSS buffer containing fetal bovine serum to complete the digestion. The mass concentration of the fetal bovine serum was 10%, and the temperature of the HBSS buffer was 4° C.

In some embodiments of this invention, the digestion was terminated by using the Hanks solution containing fetal bovine serum. The mass concentration of the fetal bovine serum was 10%, and the temperature of the Hanks solution was 4° C.

In some specific embodiments of this invention, the digestion reagent contains DNase, Collagenase V and Collagenase IV.

Specifically, the enzyme activity unit of the DNase was 15. The volume of the Collagenase V was equal to the volume of the Collagenase IV, and the concentration was both 1 mg/ml.

In the examples 1-3 of this invention, after the digestion was completed, the digested products obtained by the digestion were filtered by using a mesh with a pore size of 150 μm. Then, the filtered digested products were centrifuged under a centrifugal force of 1000 g for 3 minutes to get the precipitates, which were resuspended with a demixing agent to obtain a cell suspension.

In the step S2 of the embodiment of this invention, in order to ensure that most of the obtained primary cells were pancreatic ductal epithelial cells, so as to improve the yield of the pancreatic precursor-like cells. Therefore, it was necessary to collect the cell clusters at each density gradient junction. Afterwards, the islet cells and acinar cells in the cell clusters were removed.

In the step S2 of the embodiment of this invention, at least three demixing agents with different densities were used to perform the discontinuous density gradient centrifugation treatment, and the adjacent demixing agents were low-density demixing agent and high-density demixing agent, respectively. The density of the low-density demixing agent was reduced by 0.1-3% relative to the high-density demixing agent. It was beneficial to make most of the pancreatic ductal epithelial cells exist at the junction between adjacent density gradients.

Further, among the demixing agents with different densities, the highest density of the demixing agent was not higher than 1.1 g/ml, and the lowest density of the demixing agent was not lower than 1.03 g/ml.

In some embodiments of this invention, the demixing agent was Percoll cell separation solution.

In example 1 of this invention, three kinds of the Percoll cell separation solutions with densities of 1.075 g/ml, 1.045 g/ml, and 1.035 g/ml were prepared, and they were added to the centrifuge tube in sequence. Next, the cell suspension obtained by resuspension was put into the centrifuge tube to obtain pre-centrifuged suspension. The pre-centrifuged suspension was performed the discontinuous density gradient centrifugation treatment for 15 minutes at 4° C. with a centrifugal force of 2500 g, and the acceleration rate of 3 m/s$^2$ and the deceleration rate of 0 m/s$^2$ were controlled.

In some specific embodiments of this invention, the volumes of the Percoll cell separation solutions of each density were the same and twice the volume of the pre-centrifuged suspension.

In the example 1 of this invention, the volumes of the Percoll cell separation solutions of each density were 10 ml, and the volumes of the pre-centrifuged suspension were 5 ml.

In some embodiments of this invention, the demixing agent was Ficoll cell separation solutions.

In example 2 of this invention, four kinds of the Ficoll cell separation solutions with densities of 1.088 g/ml, 1.076 g/ml, 1.066 g/ml, and 1.040 g/ml were prepared, and they were added to the centrifuge tube in sequence. Next, the cell suspension obtained by resuspension was put into the centrifuge tube to obtain pre-centrifuged suspension. The pre-centrifuged suspension was performed the discontinuous density gradient centrifugation treatment for 20 minutes at 4° C. with a centrifugal force of 3000 g, and the acceleration rate of 3 m/s² and the deceleration rate of 0 m/s² were controlled.

In example 3 of this invention, four kinds of the Ficoll cell separation solutions with densities of 1.1 g/ml, 1.080 g/ml, 1.060 g/ml, and 1.040 g/ml were prepared.

In the example 2 and 3 of this invention, the volume of the Ficolls with each density was 10 ml, and the volume of the pre-centrifuged suspension was 5 ml.

In the step S2 of the embodiment of this invention, the cell clusters at the junction between adjacent density gradients comprise ductal epithelial cells, islet cells, acinar cells, and other types of ductal cells. Hence, the islet cells and the acinar cells in the cell clusters needed to be further removed to ensure that most of the primary cells obtained were pancreatic ductal epithelial cells.

In some embodiments of this invention, after the cell clusters were stained with dithizone (DTZ), the islet cells appearing red or scarlet and the acinar cells appearing grape bunches were manually removed under a microscope. The specific dyeing and removed methods were conventional technical means of those skilled in the art and will not be repeated here.

In the step S3 of the embodiment of this invention, the amplifying medium comprises a reprogramming substance composed of several small molecule compounds, and the reprogramming substance comprises a growth factor, a Rock signal pathway inhibitor, a WNT signal pathway agonist, and a TGF-β signal pathway inhibitor. The pancreatic precursor-like cells can be obtained by inducing the reprogramming of the primary cells, which avoids the risks of non-specific and off-target deletion that were easily caused by the use of gene-editing methods to change the gene sequence.

In the step S3 of some embodiments of this invention, the primary cells were seeded in a pre-coated culture dish with Matrigel and cultured for 48 hours. Afterwards, the amplifying medium was used to performed amplifying treatment continuously.

In some embodiments of this invention, the amplifying medium was composed of a basic medium, serum, a serum-free neuron supplement and the reprogramming substance. In the amplifying medium, the total volume percentage of the serum and the serum-free neuron supplement was not higher than 15%.

In some embodiments of this invention, the volume percentage of the serum in the amplifying medium was 2-10%.

In some embodiments of this invention, the basic medium was at least one of MEM, DMEM, BME, DMEM/F12, RPMI1640, CMRL1066, WilliamE, Neurobasal, and Fischers medium.

In some embodiments of this invention, the serum was fetal bovine serum. The serum-free neuron supplement was at least one of the N2 supplement and B27 supplement.

In some embodiments of this invention, the growth factor includes epidermal growth factor, hepatocyte growth factor, and fibroblast growth factor to facilitate the development of the primary cells. In the amplifying medium, the contents of the epidermal growth factor, the human hepatocyte growth factor, and the human fibroblast growth factor were all 5-100 ng/ml.

In some embodiments of this invention, the epidermal growth factor was the human epidermal growth factor. The hepatocyte growth factor was human hepatocyte growth factor. The fibroblast growth factor was human fibroblast growth factor.

In the amplifying medium of some embodiments of this invention, the content of the Rock signal pathway inhibitor was 2-15 mmol/L.

Specifically, the Rock signal pathway inhibitor was at least one of Y27632, Fasudil, Thiazovivin, and SB-772077-B.

In the amplifying medium of some embodiments of this invention, the content of the WNT signal pathway agonist was 2-10 μmol/L.

Specifically, the WNT signal inhibitor was at least one of recombinant Wnt protein, recombinant R-spondin protein, and glycogen synthase kinase 3β inhibitor. The glycogen synthase kinase 3β inhibitor was at least one of the BIO, CHIR99021, and TWS119.

In the amplifying medium of some embodiments of this invention, the content of the TGF-β signal pathway inhibitor was 0.5-20 μmol/L.

Specifically, the TGF-β signal pathway inhibitor was at least one of A83-01, RepSox and SB431542.

In some embodiments of this invention, the amplifying medium further includes a lipid signal substance, and the content of the lipid signal substance was 0.5-10 μmol/L.

Specifically, the lipid signal substance was at least one of sphingosine-1-phosphate and lysophosphatidic acid.

In the example 1 of this invention, the amplifying medium was composed of DMEM/F12, fetal bovine serum, N2 supplement, B27 supplement, human epidermal growth factor, human hepatocyte growth factor, human fibroblast growth factor, Y27632, CHIR99021, A83-02, sphingosine-1-phosphate, and lysophosphatidic acid.

Specifically, in the amplifying medium, the content of the human hepatocyte growth factor was 20 ng/ml. The content of the human hepatocyte growth factor was 20 ng/ml. The content of the human fibroblast growth factor was 20 ng/ml. The content of the Y27632 was 10 μmol/L. The content of the CHIR99021 was 3 μmol/L. The content of the sphingosine-1-phosphate was 1 μmol/L. The content of the lysophosphatidic acid was 5 μmol/L. The content of the A83-01 was 1 μmol/L. The volume percentage of the fetal bovine serum was 2%. The volume percentage of the N2 supplement was 0.5%. The volume percentage of the B27 supplement was 1%.

The amplifying medium of the example 2 of this invention was composed of DMEM/F12, fetal bovine serum, N2 supplement, B27 supplement, human epidermal growth factor, human fibroblast growth factor, human hepatocyte growth factor, Thiazovivin, BIO, and A83-01.

Specifically, in the amplifying medium of example 2 of this invention, the content of the human epidermal growth factor was 20 ng/ml. The content of the human fibroblast growth factor was 20 ng/ml. The content of the Thiazovivin was 2 μmol/L. The content of the BIO was 10 μmol/L. The content of the A83-01 was 1 μmol/L. The volume percentage of the fetal bovine serum was 5%. The volume percentage of the N2 supplement was 0.5%. The volume percentage of the B27 supplement was 1%.

The amplifying medium of example 3 of this invention was composed of DMEM/F12, fetal bovine serum, N2 supplement, B27 supplement, human epidermal growth factor, human fibroblast growth factor, human hepatocyte growth factor, Y27632, CHIR99021, and SB431532.

Specifically, in the amplifying medium of example 3 of this invention, the content of the human epidermal growth factor was 20 ng/ml. The content of the hepatocyte growth factor was 20 ng/ml. The content of the Y27632 was 10 μmol/L. The content of the CHIR99021 was 3 μmol/L. The content of the SB431532 was 10 μmol/L. The volume percentage of the fetal bovine serum was 5%. The volume percentage of the N2 supplement was 0.5%. The volume percentage of the B27 supplement was 1%.

In control example 1 of the embodiment of this invention, the amplifying medium was composed of DMEM/F12, epidermal growth factor, fetal bovine serum, transferrin, and insulin. The volume percentage of the fetal bovine serum was 10%. The content of the human epidermal growth factor was 20 ng/ml. The content of the transferrin was 5 μg/ml. The content of the insulin was 10 μg/ml.

In the example 1 and the control example 1 of this invention, the period of the amplifying treatment was at least 72 hours, and the amplifying medium was replaced every 48 hours after the cells adhere. Except for the difference in the composition of the amplifying medium, the other operations of steps S1 to S3 were the same.

In the example 1 of this invention, the removal extent of the islet cells and the acinar cells in the cell clusters was investigated. The primary cells were performed a static culture with the amplifying medium for 3 days, and most of the cells adhered to the culture dish and flattened into a single cell layer was found. The cells were performed RT-PCR technology to detect the expression of related genes. The specific detection methods were referred to CN108330099A and will not be repeated here.

Specifically, the primary cells significantly express HNF1B with expression level of 3000, CK19 with expression level of 300,000, and FOXA2 with expression level of 10,000. While among the genes related to the acinar cells and the islet cells, only HNF1 and INS were expressed, the expression level were all lower than 100, which was almost negligible. It was indicated that the islet cells and the acinar cells in the primary cells can be negligible mostly.

Figure 2:
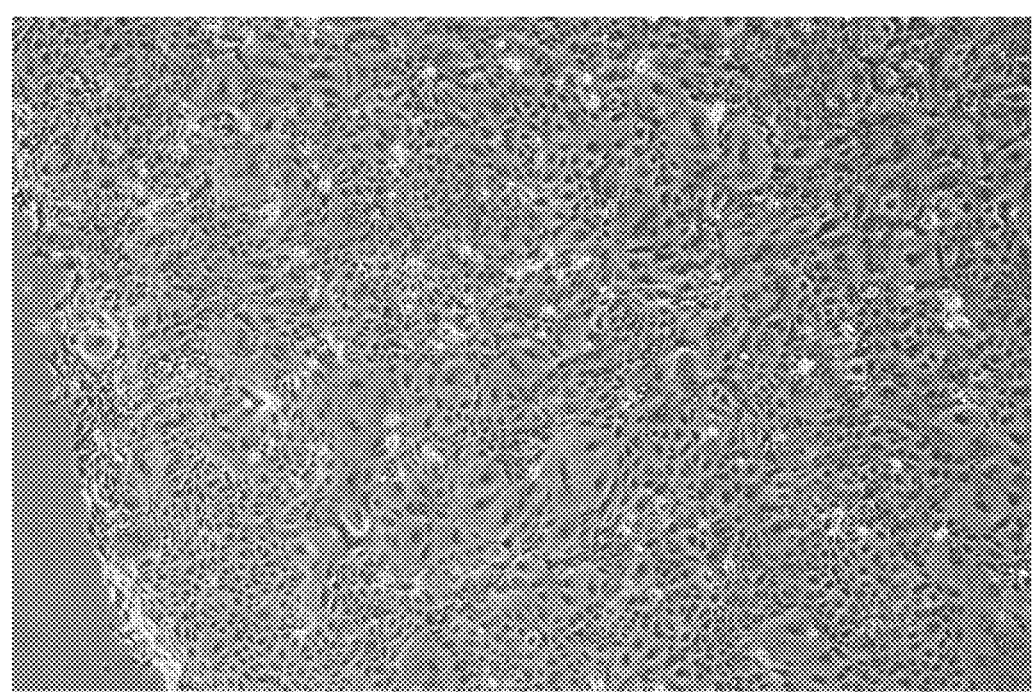
FIG. 2 is a photo of the proliferation of the primary cells shown in FIG. 1 on $7^{th}$ day after adding the amplifying medium.
Figure 3:
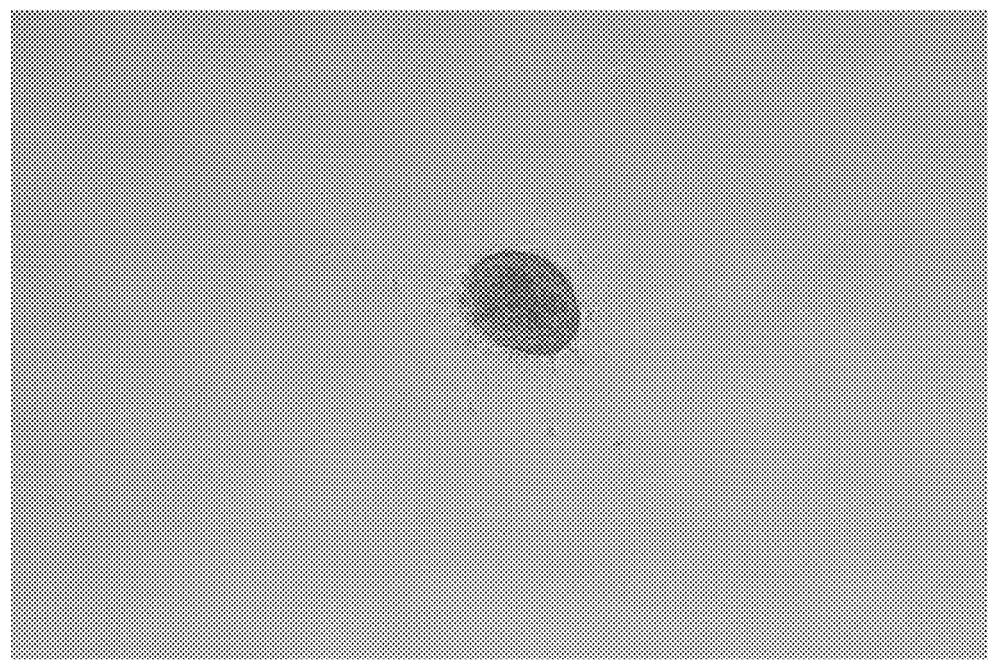
FIG. 3 is a photo of the proliferation of the primary cells of a control example of this invention on $1^{st}$ day after adding the amplifying medium.
Figure 4:
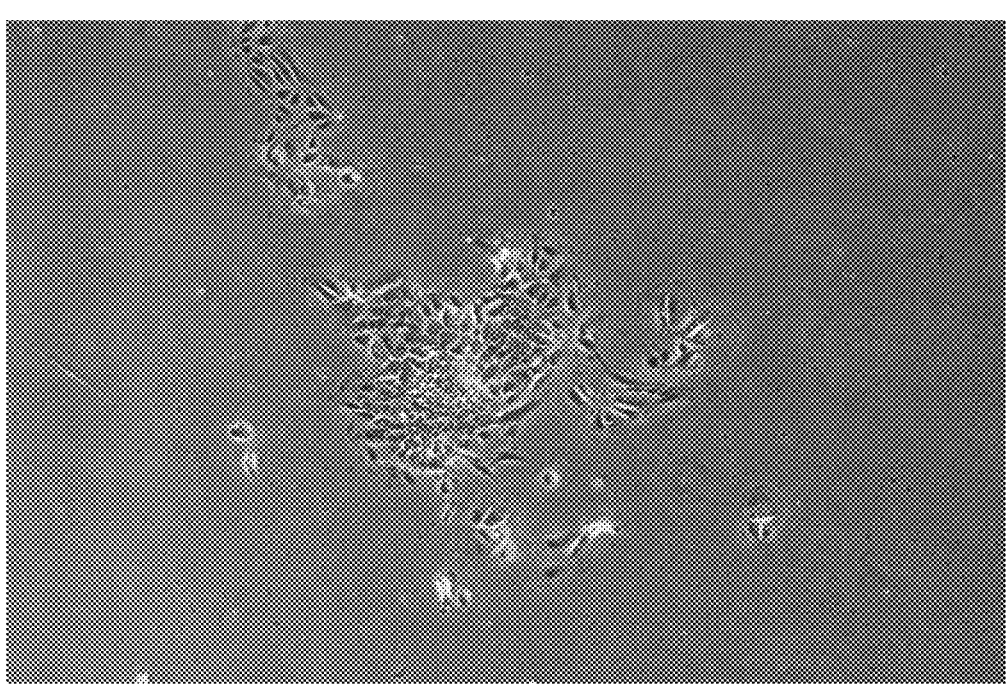
FIG. 4 is a photo of the proliferation of the primary cells shown in FIG. 3 on $7^{th}$ day after adding the amplifying medium.

FIG. 1 and FIG. 2 were photos of the proliferation of the primary cells of example 1 of this invention on the first and seventh days after adding the amplifying medium. FIG. 3 and FIG. 4 were photos of the proliferation of the primary cells of control example 1 of this invention on the first and seventh days after adding the amplifying medium of this invention.

Referring to FIG. 1 and FIG. 2, the primary cells of example 1 of this invention show significant proliferation after adding the amplifying medium and significant amplification on the seventh day.

Referring to FIG. 3 and FIG. 4, the primary cells of control example 1 did not proliferate significantly on the first day after adding the amplifying medium, and did not show significant expansion until the seventh day. It can be presented that the amplifying medium of the embodiments of this invention can endow the primary cells with a strong amplifying ability, which was beneficial to solve the problem of low yield of replacement cells of islet cells.

The examples 1-3 of this invention respectively investigated the proliferation performance of the pancreatic precursor-like cells, and further investigated the proliferation state of the pancreatic precursor-like cells proliferated to the tenth generation through the EdU proliferation assay.

Specifically, 5000 pancreatic precursor-like cells to be investigated were seeded in a six-well plate pre-coated with Matrigel and allowed to stand for 24 hours. Then, the cells were digested and counted by a countstar to calculate the doubling time.

In the Edu infiltration assay, BeyoClickTMEdU-488 cell proliferation detection kit from Beyotime Biotechnology Co., Ltd. was used to stain the tenth-generation cells, and the nuclei were marked by Hoechst33342, and then photographed with a Nikon Ts2-FL fluorescent inverted microscope.

Figure 5:
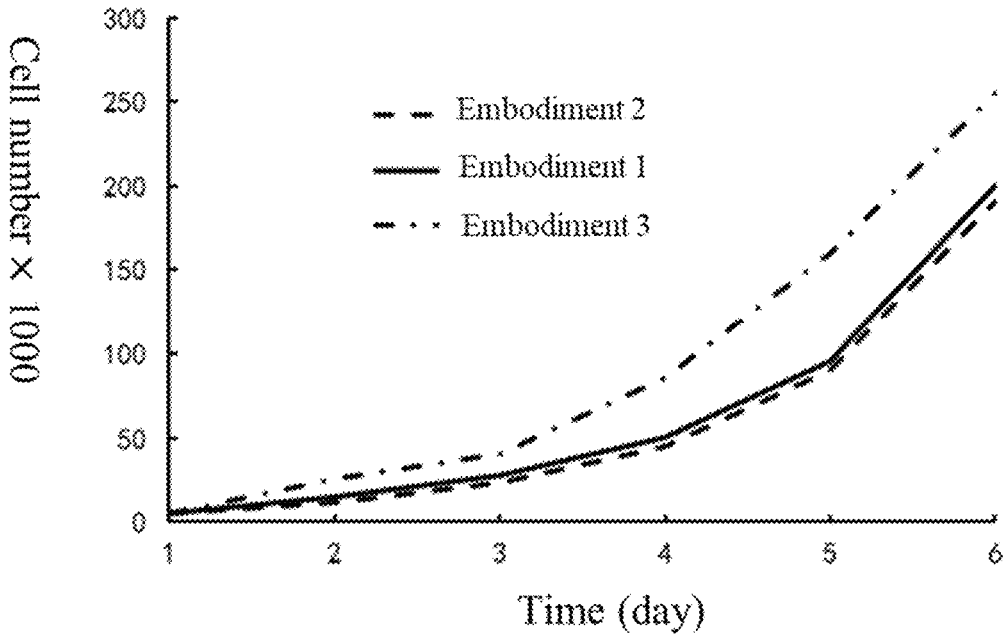
FIG. 5 is a comparative schematic diagram of the proliferation performance of the three pancreatic cells of the examples of this invention.

FIG. 5 was a comparative schematic diagram of the proliferation performance of the pancreatic precursor-like cells of examples 1-3 of this invention.

Referring to FIG. 5, the proliferation performance of the pancreatic precursor-like cells of the examples 1-3 shown in FIG. 5 shows that the doubling times of the pancreatic precursor-like cells of the examples 1, 2, and 3 were 14 hours, 15 hours, and 12 hours, respectively. It can be seen that the three types of the pancreatic precursor-like cells have good proliferation ability.

Figure 6:
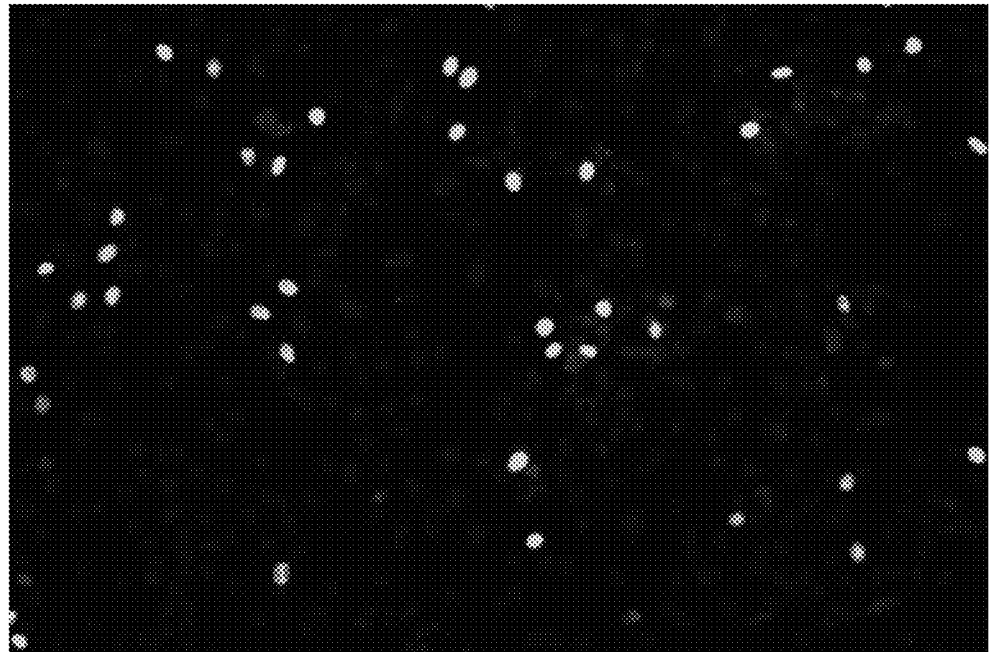
FIG. 6 is a photo of the proliferation state of the pancreatic-like cells of an embodiment of this invention proliferated to the $10^{th}$ generation.

FIG. 6 was a photo of the proliferation state of the pancreatic-like cells proliferated to the tenth generation of example 1 of this invention. It can be seen that the pancreatic precursor-like cells have proliferated to at least the tenth generation and can still remain active proliferation state.

In the examples 1-3 of this invention, the passage numbers of each type of the pancreatic precursor-like cells were 15, 16 and 22, respectively.

In the examples 1-3 of this invention, the tenth-generation cells formed by the proliferation of each pancreatic precursor-like cells were incubated with 100 ng/ml colchicine at 37° C. for 40 minutes, and then the obtained culture was washed. The washed culture was dissociated into single cells by Accutase cell detachment solution for karyotype analysis and counted the chromosomes of at least 40 metaphase arrest cells. The karyotype analysis was performed in the karyotype analysis department of Jidi Gene Technology (Hangzhou) Co., Ltd. Wherein, the proliferation of each type of the pancreatic precursor-like cells to the tenth generation was still in the exponential growth phase. The result of the karyotype analysis found that the cells can still remain a stable diploid karyotype without mutation.

In examples 1-3 of this invention, the expression levels of stem cell-related markers of each type of the pancreatic precursor-like cells obtained on the fifth and ninth day after adding the amplifying medium were investigated by flow cytometry.

On one hand, EpCAM, Pdx1, and Krt19 were significantly expressed on the fifth and ninth days after adding the amplifying medium. It was indicated that the pancreatic precursor-like cells obtained in the embodiments of this invention obtained part of the precursor cells characteristic. Please refer to CN108330099A for the specific operation of the flow cytometry, which will not be repeated here.

Specifically, for example, the proportion of positive cells expressing stem cell-related markers, such as EpCAM, Pdx1, and Krt19, was counted by flow cytometry on the fifth day after adding the amplifying medium, which was 99.2±0.7%, 74.8±2.3%, and 92.0±4.7%, respectively.

On the other hand, Table 1 shows the average expression levels of the pancreatic precursor-like cells of examples 1-3 of this invention that express acinar-related markers, endocrine-related markers, and duct or precursor-related markers, compared with pancreatic tissue. The specific statistical method was the common technical means of those skilled in the art.

TABLE 1

| | Marker | Pancreatic precursor-like cells | Pancreatic tissue |
|---|---|---|---|
| acinar-related | Ptf1a | 3.11E–3 ± 1.24E–3 | 1.02E+0 ± 2.21E–1 |
| | Gata4 | 1.71E–2 ± 3.34E–3 | 1.00E+0 ± 7.25E–2 |
| | Cpa1 | 1.50E–5 ± 6.64E–6 | 1.03E+0 ± 2.27E–1 |
| endocrine-related | Nkx2.2 | 7.36E–2 ± 1.34E–2 | 1.01E+0 ± 4.65E–1 |
| | Mafb | 4.05E–2 ± 1.31E–2 | 1.00E+0 ± 3.73E–2 |
| | Gcg | 3.82E–3 ± 5.26E–4 | 1.00E+0 ± 9.69E–2 |
| | Sst | 8.58E–3 ± 1.98E–3 | 1.00E+0 ± 8.48E–2 |
| | Ins | 5.32E–4 ± 1.29E–4 | 1.00E+0 ± 2.70E–2 |
| duct or precursor-related | Pdx1 | 5.91E–1 ± 1.95E–2 | 1.00E+0 ± 6.22E–2 |
| | Nkx6.1 | 2.10E–1 ± 3.15E–2 | 1.01E+0 ± 1.50E–1 |
| | Foxa2 | 8.41E–1 ± 1.60E–1 | 1.02E+0 ± 2.31E–1 |
| | Hnf1b | 1.60E–1 ± 2.92E–2 | 1.00E+0 ± 7.76E–2 |
| | Epcam | 4.00E–1 ± 1.59E–2 | 1.00E+0 ± 2.83E–2 |
| | Krt19 | 9.99E–1 ± 9.08E–2 | 2.18E–1 ± 3.70E–2 |

It can be seen from Table 2:

Compared with the expression levels of the acinar-related markers in the pancreatic tissue, specifically the expression levels of Ptf1a, Gata4, and Cpa1, the expression levels of the aforementioned acinar-related markers in the pancreatic precursor-like cells in the examples of this invention were extremely low. It was proved that the acinar cells were removed effectively in the step S2 of the examples of this invention.

Compared with the expression levels of the endocrine-related markers in the pancreatic tissue, specifically the expression levels of Nkx2.2, Math, Gcg, Sst, and Ins, the expression levels of the aforementioned endocrine-related markers in the pancreatic precursor-like cells in the examples of this invention were extremely low. It was proved that the endocrine function of the islet-like cells in the examples of this invention was indeed derived from the differentiated pancreatic precursor-like cells.

Compared with the expression levels of the duct or precursor-related markers in the pancreatic tissue, specifically the expression levels of Pdx1, Nkx6.1, Foxa2, Hnf1b, EpCAM, and Krt19, the expression levels of the aforementioned duct or precursor-related markers in the pancreatic precursor-like cells in the embodiments of this invention were not much different. It was proved that the pancreatic precursor-like cells obtained in the examples of this invention have potential to differentiate into islet-like cells with endocrine function.

The differentiation method of the pancreatic precursor-like cells in the embodiments of this invention comprises that the pancreatic precursor-like cells were seeded in a culture dish, and then induced through a differentiation medium to differentiate into islet-like cells.

In some embodiments of this invention, the differentiation medium comprises several small molecule inducers, and the several small molecule inducers comprise heparin, deacetylase inhibitor, ALK5 inhibitor, T3, and GLP-1 receptor agonist. To facilitate the targeted induction of the pancreatic precursor-like cells to differentiate into the islet-like cells with good pancreatic islet function.

In the differentiation medium of some embodiments of this invention, the content of the heparin was 5-15 μg/ml. The content of the deacetylase inhibitor was 5-15 mmol/L. The content of the ALK5 inhibitor was 5-15 μmol/L. The content of the T3 was 0.5-2 μmol/L. The content of the GLP-1 receptor agonist was 10-50 nmol/L.

In some embodiments of this invention, the differentiation medium was composed of a basic medium, a serum-free neuron supplement, and the several small molecule inducers.

In some embodiments of this invention, the deacetylase inhibitor was at least one of nicotinamide and Trichostatin A.

In some embodiments of this invention, the GLP-1 receptor agonist was at least one of GLP-1, and Exendin-4.

In some embodiments of this invention, the basic medium in the differentiation medium was at least one of MEM, DMEM, BME, DMEM/F12, RPMI1640, CMRL1066, WilliamE, Neurobasal, and Fischers medium.

In some specific embodiments of this invention, the serum-free neuron supplement in the differentiation medium was at least one of N2 supplement and B27 supplement.

In the example 1 of this invention, the differentiation medium was composed of DMEM/F12, N2 supplement, B27 supplement, nicotinamide, heparin, ALK5 inhibitor II, T3, and GLP-1.

Specifically, in the differentiation medium, the volume percentage of the N2 supplement and B27 supplement were both 5%. The content of the nicotinamide was 10 mmol/L. The content of the heparin was 10 μg/ml. The content of the ALK5 inhibitor II was 10 mmol/L. The content of the T3 was 1 μmol/L. The content of the GLP-1 was 30 nmol/L.

The differentiation medium of the example 2 and 3 of this invention has the same material composition as the differentiation medium of the example 1.

In the differentiation medium of example 2 of this invention, the volume percentage of the N2 supplement and B27 supplement were both 3%. The content of the nicotinamide was 5 mmol/L. The content of the heparin was 5 μg/ml. The content of the ALK5 inhibitor II was 5 mmol/L. The content of the T3 was 0.5 μmol/L. The content of the GLP-1 was 10 nmol/L.

In the differentiation medium of example 3 of this invention, the volume percentage of the N2 supplement and B27 supplement were both 10%. The content of the nicotinamide was 15 mmol/L. The content of the heparin was 15 μg/ml. The content of the ALK5 inhibitor II was 15 mmol/L. The content of the T3 was 2 μmol/L. The content of the GLP-1 was 50 nmol/L.

In the example 1-3 of this invention, the period of differentiation culture was 7-10 days, and the differentiation medium was replaced every 48 hours.

Figure 7:
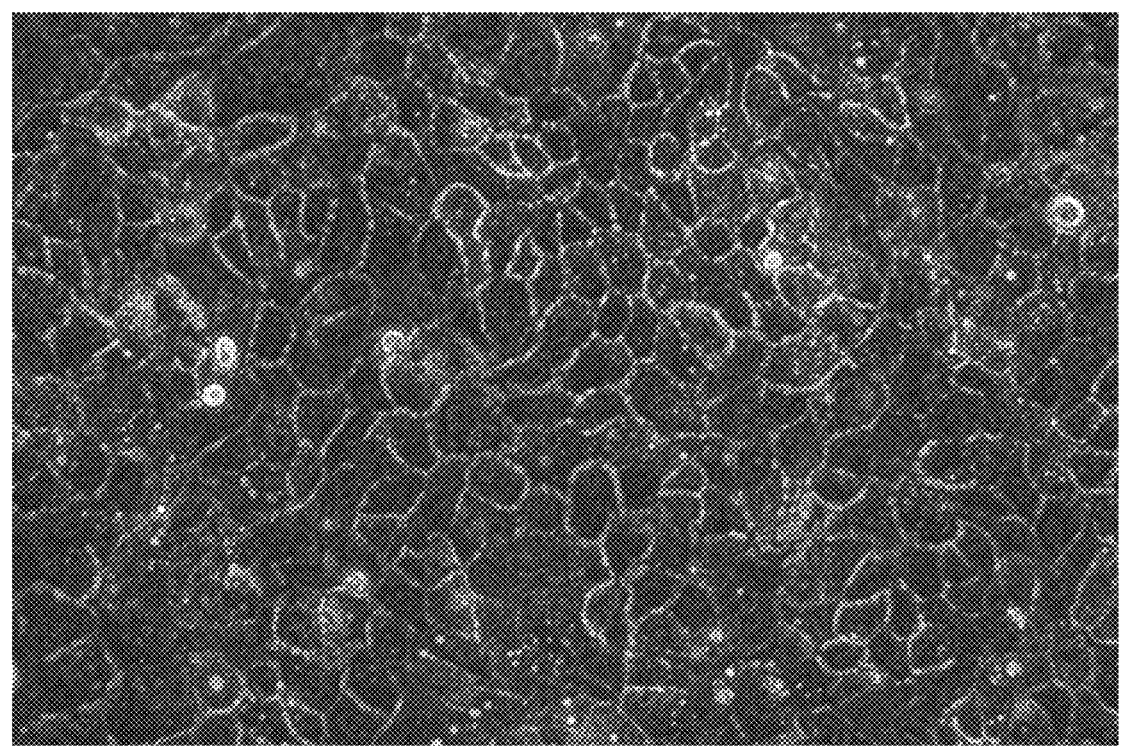
FIG. 7 is a microscopic diagram of the morphology of the islet-like cells of an embodiment of this invention at a magnification of 100 times.

FIG. 7 was a microscopic diagram of the morphology of the islet-like cells at a magnification of 100 times of example 1 of this invention. Referring to FIG. 7, the islet-like cells present a clear outline, and the outline shape was similar to a polygon.

In examples 1-3 of this invention, GAPDH was used as an internal reference gene, and the Q-PCR method was used to detect the gene levels of CK19, SOX9, NKX2-2, PDX1, INS, GCG, SST, and MAFA of each type of the pancreatic precursor-like cells and the corresponding islet-like cells.

On one hand, at the mRNA level, compared with undifferentiated pancreatic precursor-like cells, the expression levels of the precursor-related genes of the islet-like cells, such as CK19 and SOX9, were decreased.

Taking example 1 as an example, the expression level of CK19 was decreased by 80%, and the expression level of SOX9 was decreased by 30%.

On the other hand, at the mRNA level, compared with undifferentiated pancreatic precursor-like cells, the expression of mature islet-related genes, such as PDX1, NKX2-2, MAFA, INS, GCG, and SST, were significantly upregulated.

Taking the example 1 as an example, the expression level of PDX1 was upregulated by 110%, the expression level of NKX2-2 was upregulated by 300%, the expression level of MAFA was upregulated by 200%, the expression level of INS was upregulated by 350%, the expression level of GCG was upregulated by 220%, and the expression level of SST was upregulated by 900%.

Further, the islet-like cells of examples 1-3 were subjected to an in vitro insulin-stimulated secretion experiment to investigate the islet function of the islet-like cells.

First, a low-sugar Krb buffer, a high-sugar Krb buffer, and a Krb stimulated buffer were prepared through Krb buffer. The $1\times10^6$ islet-like cells were taken and washed twice with the Krb buffer. Afterwards, the islet-like cells were incubated in the low-sugar Krb buffer for one hour for equilibrating. Next, after the islet-like cells were washed with the Krb buffer, the islet-like cells were placed in the low-sugar Krb buffer for 30 minutes to complete the first stimulation. The supernatant was removed and the islet-like cells were washed twice with the Krb buffer, and the islet-like cells were incubated in the high-sugar Krb buffer for 30 minutes to complete the second stimulation. Then, the supernatant was removed again and the islet-like cells were washed twice with the Krb buffer. Finally, the obtained cells were incubated in the Krb stimulated buffer for 30 minutes, and the supernatant was removed finally to complete the third stimulation. The cells obtained from each stimulation were digested with TrypLE and counted by countstar.

Specifically, the Krb buffer comprises 128 mM NaCl, 5 mM KCl, 2.7 mM CaCl$_2$, 1.2 mM MgCl$_2$, 1 mM Na$_2$HPO$_4$, 1.2 mM KH$_2$PO$_4$, 5 mM NaHCO$_3$, 10 mM HEPES, and 0.1% BSA.

In the low-sugar Krb buffer, the concentration of glucose was 2 mmol/L. In the high-sugar Krb buffer, the concentration of glucose was 20 mmol/L. In the Krb stimulated buffer, the concentration of glucose was 2 mmol/L, and the concentration of KCl was 30 mmol/L.

The in vitro insulin stimulation and secretion experiment showed that for the islet-like cells of example 1, the insulin contents of every $10^3$ islet-like cells obtained after the first stimulation, the second stimulation, and the third stimulation were 0.6 μU/ml, 1 μU/ml, and 1.5 μU/ml, respectively.

For the islet-like cells of example 2, the insulin contents of every $10^3$ islet-like cells obtained after the first stimulation, the second stimulation, and the third stimulation were 0.5 μU/ml, 1.3 μU/ml, and 1.5 μU/ml, respectively.

For the islet-like cells of example 3, the insulin contents of every $10^3$ islet-like cells obtained after the first stimulation, the second stimulation, and the third stimulation were 0.9 μU/ml, 0.7 μU/ml, and 2.2 μU/ml, respectively.

Additionally, taking example 1 as an example, the stimulation index calculated from the ratio of insulin secreted by the high-sugar Krb buffer to insulin secreted by the low-sugar Krb buffer was 2.2±0.4.

In summary, the stated experimental results of the in vitro insulin stimulation and secretion experiment, it can be seen that the islet-like cells applied to the in vitro high-glucose reagent can effectively secrete insulin. The islet-like cells have the potential to differentiate into islet cells.

The examples 1-3 of this invention, the islet-like cells were applied to animal model to investigate the change rate of body weight and the blood sugar of the experimental animals.

Specifically, Streptozocin, STZ, was dissolved in a 1% concentration of the citric acid buffer to form an injection solution. After the NGS severely immunodeficient mice were weighed, they were injected intraperitoneally with the injection solution 130 mg/kg. One week after the injection, if the blood sugar of the NGS severely immunodeficient mice was ≥20 mM, it was considered that the NSG type I diabetes model has established. The $1\times10^6$ islet-like cells

14 were mixed with appropriate amount of Matrigel and transplanted under the renal capsule of the successfully modeled NSG severely immunodeficient mice. Then, the NSG severely immunodeficient mice were recovered for one week to complete the transplantation experiment. After the transplantation experiment was completed, the blood sugar value and body weight of the NSG severely immunodeficient mice were monitored.

The embodiment of this invention also provides control example 2. After the NSG severely immunodeficient mice were injected intraperitoneally with the injection solution 130 mg/kg, the Matrigel was transplanted under the renal capsule of the successfully modeled NSG severely immunodeficient mice. The rest of the process applied to the animal model was the same as in examples 1-3.

Figure 8:
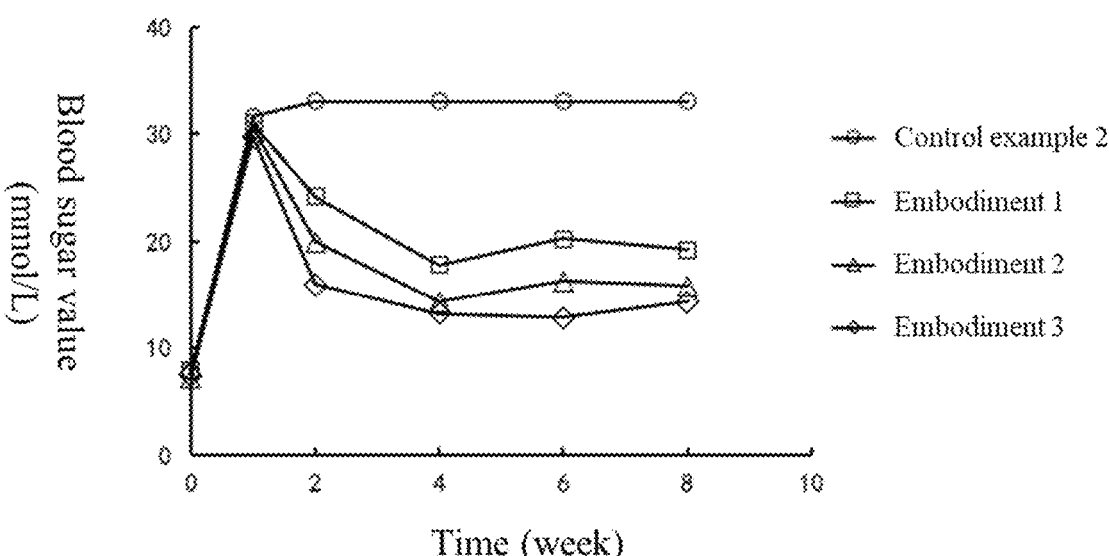
FIG. 8 is a curve diagram showing the changes in blood sugar values with time of different NSG severely immunodeficient mice of the embodiments and the control example of this invention after completing the transplantation experiment.
Figure 9:
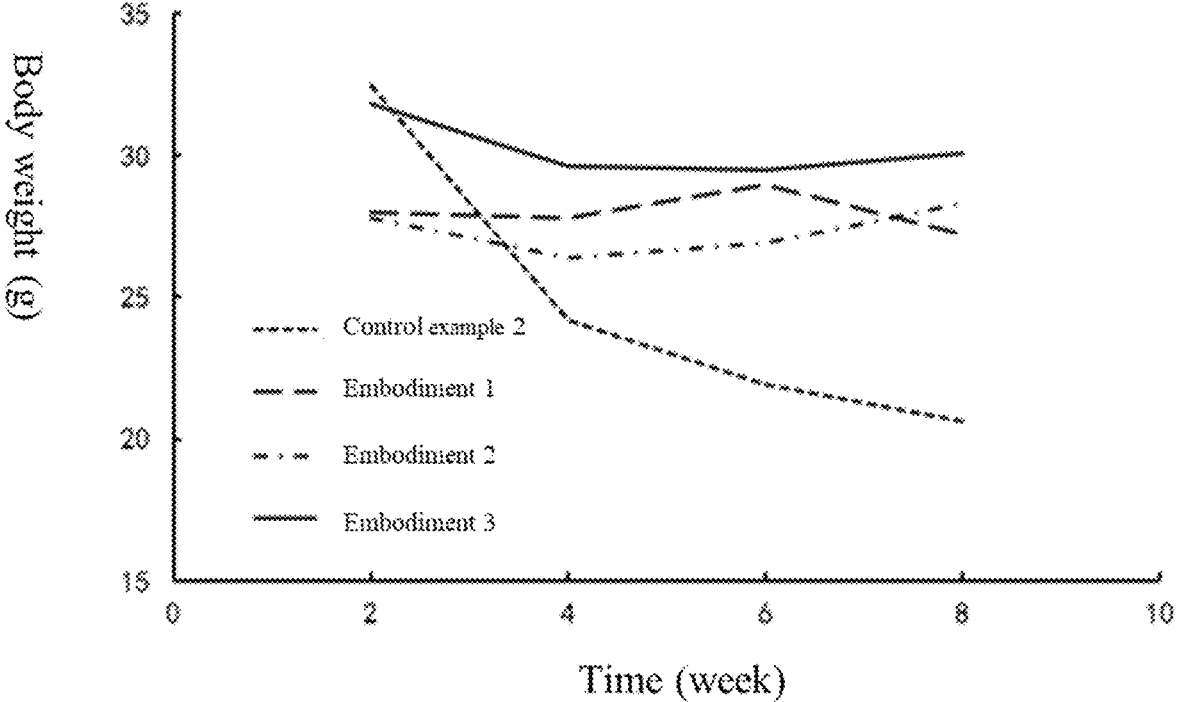
FIG. 9 is a curve diagram showing the weight changes with time of different NSG severely immunodeficient mice of the embodiments and the control example of this invention after completing the transplantation experiment.

FIG. 8 and FIG. 9 are curve diagrams showing the changes in the blood sugar values and body weight with time of the NSG severely immunodeficient mice of examples 1-3 and control example 2 at the second, fourth, sixth, and eighth week after the completion of the transplantation experiment respectively. It can be seen that within 8 weeks after the completion of the transplantation experiment, the body weight change rate of the animal model of the examples 1-3 was ±5%, and the blood sugar value was 10-20 mmol/L. It was indicated that islet-like cells of the embodiments of this invention can effectively assist to control blood sugar and body weight.

Although the embodiments of this invention were described in detail above, it was obvious to those skilled in the art that various modifications and changes can be made to these embodiments. However, it should be understood that such modifications and changes fall within the scope and spirit of this invention described in the claims. Moreover, this invention described here may have other embodiments and may be implemented or realized in various ways.

What is claimed is:

1. An amplifying method of pancreatic cells, comprising:
   S1: obtaining pancreatic tissue, derived from a mammalian pancreatic duct;
   S2: performing digestion, resuspension, and discontinuous density gradient centrifugation treatment to the pancreatic tissue in sequence, collecting the cell clusters at each density gradient junction, and then removing islet cells and acinar cells in the cell clusters to obtain primary cells;
   S3: performing an amplifying and adhering treatment to the primary cells with an amplifying medium to induce reprogramming of the primary cells to obtain pancreatic precursor-like cells;
   wherein a period of the amplifying treatment was at least 72 hours, and the amplifying medium was replaced every 48 hours after the cells are adhered to a culture dish by the adhering treatment;
   wherein the amplifying medium comprising a reprogramming substance composed of several small molecule compounds, and the reprogramming substance comprises growth factor, Rock signal pathway inhibitor, WNT signal pathway agonist and TGF-β signal pathway inhibitor,
   in the step S2, at least three demixing agents with different densities are used to perform the discontinuous density gradient centrifugation treatment, the adjacent demixing agents are a low-density demixing agent and a high-density stratification, and the density of the low-density demixing agent is decreased by 0.1-3% relative to the density of the high-density demixing agent, and wherein the highest density of the demixing agents is not higher than 1.1 g/ml, and the lowest density of the demixing agents is not less than 1.03 g/ml;

wherein the pancreatic precursor like cells are formed in a single cell layer by adhering to the culture dish in the adhering treatment, and the pancreatic precursor like cells of the single cell layer can be proliferated until the 10th generation and be still in an exponential growth phase.

2. The amplifying method of claim 1, wherein the pancreatic tissue is derived from a human pancreatic duct.

3. The amplifying method of claim 1, wherein the growth factor comprises at least one of epidermal growth factor, hepatocyte growth factor, and fibroblast growth factor, wherein a content of any one of the epidermal growth factor, the hepatocyte growth factor, and the fibroblast growth factor is 5-100 ng/ml in the amplifying medium.

4. The amplifying method of claim 1, wherein a content of the Rock signal pathway inhibitor is 2-15 μmol/L, a content of the WNT signal pathway agonist is 2-10 μmol/L, and a content of the TGF-β signal pathway inhibitor is 0.5-20 μmol/L in the amplifying medium.

5. The amplifying method of claim 4, wherein the Rock signal pathway inhibitor is at least one of Y27632, Fasudil, Thiazovivin, and SB-772077-B; the WNT signal pathway agonist is at least one of recombinant WNT protein, recombinant R-spondin protein, and glycogen synthase kinase 3β inhibitor; the glycogen synthase kinase 3β inhibitor is at least one of BIO, CHIR99021, and TWS119; the TGF-β signal pathway inhibitor is at least one of A83-01, RepSox, and SB431542.

6. The amplifying method of claim 1, wherein the amplifying medium further comprises a basic medium, serum, and serum-free neuron supplement; in the amplifying medium, the total volume of the serum and the serum-free neuron supplement is not higher than 15%, and the volume percentage of the serum is 2% to 10%.

7. The amplifying method of claim 6, wherein the reprogramming substance further comprise a lipid signal substance having a content of 0.5-10 μmol/L in the amplifying medium.

8. The amplifying method of claim 7, wherein the lipid signal substance is at least one of sphingosine-1-phosphate and lysophosphatidic acid.

9. The amplifying method of claim 6, wherein the basic medium is at least one of MEM, DMEM, BME, DMEM/F12, RPMI1640, CMRL1066, WilliamE, Neurobasal, and Fischers medium; the serum is fetal bovine serum; and the serum-free neuron supplement is at least one of N2 supplement and B27 supplement.

* * * * *